US 8,372,412 B2

United States Patent
Sharma et al.

(10) Patent No.: US 8,372,412 B2
(45) Date of Patent: Feb. 12, 2013

(54) BIOASSAY AND PEPTIDES FOR USE THEREIN

(75) Inventors: Ram P. Sharma, Southampton (GB); Amit P. Mehrotra, Southampton (GB)

(73) Assignee: Rapid Biosensor Systems Limited, Cambridge (GB)

( * ) Notice: Subject to any disclaimer, the term of this patent is extended or adjusted under 35 U.S.C. 154(b) by 1149 days.

(21) Appl. No.: 12/158,781

(22) PCT Filed: Dec. 22, 2006

(86) PCT No.: PCT/GB2006/004931
§ 371 (c)(1),
(2), (4) Date: Oct. 21, 2008

(87) PCT Pub. No.: WO2007/072063
PCT Pub. Date: Jun. 28, 2007

(65) Prior Publication Data
US 2012/0115168 A1     May 10, 2012

(30) Foreign Application Priority Data

Dec. 23, 2005  (GB) .................................. 0526273.8

(51) Int. Cl.
*A61K 39/04*     (2006.01)
*A61K 39/395*    (2006.01)
*A61K 38/00*     (2006.01)

(52) U.S. Cl. ................ 424/248.1; 424/130.1; 424/139.1; 424/164.1; 424/184.1; 424/185.1; 424/234.1; 530/300; 530/350; 536/23.7

(58) Field of Classification Search ............... 424/130.1, 424/139.1, 164.1, 184.1, 185.1, 234.1, 248.1; 530/300; 536/23.7
See application file for complete search history.

(56) References Cited

U.S. PATENT DOCUMENTS

| 6,033,904 | A | 3/2000 | Cochran et al. |
| 6,245,331 | B1 | 6/2001 | Laal et al. |
| 6,599,510 | B1 * | 7/2003 | Horwitz et al. ............ 424/248.1 |
| 6,818,223 | B2 * | 11/2004 | Horwitz et al. ............ 424/248.1 |
| 2002/0131975 | A1 | 9/2002 | Horwitz et al. |

FOREIGN PATENT DOCUMENTS

| EP | 2005-525090 A | 12/2004 |
| EP | 1491553 | 12/2004 |
| WO | 93/12227 | 6/1993 |
| WO | 96/37219 | 11/1996 |
| WO | 00/73345 | 12/2000 |
| WO | 03/038444 | 5/2003 |
| WO | 2004/108948 | 12/2004 |
| WO | 2005-525090 A2 | 8/2005 |

OTHER PUBLICATIONS

Ya-Lan Pao et al., "Effect of Serine O-Glycosylation on Cis-trans Proline Isomerization", Biochemical and Biophysical Research Communications, 1996, vol. 219, 157-162.
Mustafa et al., "Infection & Immunity", 1999, vol. 67, 5683-5689.
Kashyap et al., "Clinical & Diagnostic Laboratory Immunology", 2005, vol. 12, 752-758.
D'souza et al., "Infection & Immunity", 2003, vol. 71, 483-493.
Mustafa et al., "Identification and HLA Restriction of Naturally Derived Th1-Cell Epitopes from the Secreted Mustafa et al.," Identification and HLA Restriction of Naturally Derived Th1-Cell Epitopes from the Secreted *Mycobacterium tuberculosis* Antigen 85B Recognized by Antigen-Specific Human CD4+ T-Cell Lines, Infection and Immunity, vol. 68, No. 7, Jul. 2000, pp. 3933-3940.

* cited by examiner

*Primary Examiner* — Rodney P. Swartz
(74) *Attorney, Agent, or Firm* — Renner, Otto, Boisselle & Sklar, LLP

(57) ABSTRACT

The invention provides a bioassay for detection of *Mycobacterium tuberculosis* infection comprising artificially modified peptide subsequences of the T-cell epitope from *M. tuberculosis* Ag85B. Particularly preferred peptides have the form: SGGNNSPAX (SEQ ID 26), where X is Methionine (SEQ ID 18), Leucine (SEQ ID 17), Alanine (SEQ ID 15) or Valine (SEQ ID 10) and NNSPAV (SEQ ID 14). The invention also provides peptides for use in such an assay.

3 Claims, 5 Drawing Sheets

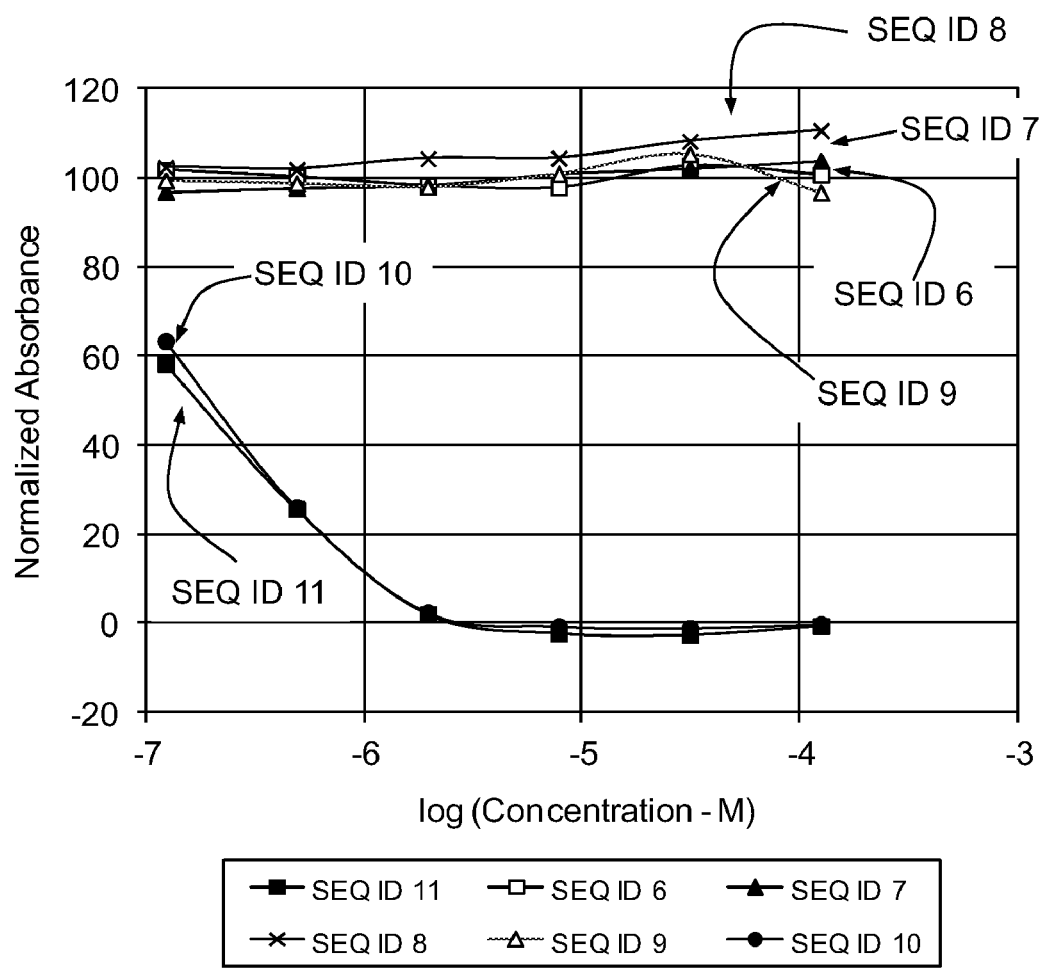

BIOASSAY AND PEPTIDES FOR USE THEREIN

This application is a national phase of International Application No. PCT/GB2006/004931 filed Dec. 22, 2006 and published in the English language.

FIELD OF THE INVENTION

The invention relates to peptides for use in an assay for the detection of *Mycobacterium tuberculosis*, and also to the assay itself.

BACKGROUND AND PRIOR ART KNOWN TO THE APPLICANT

Tuberculosis is an infection caused by the bacterium *Mycobacterium tuberculosis*. Tuberculosis is a major problem in many countries, especially in the developing world, and is on the increase in many developed countries. Whilst tuberculosis often presents as a lung infection, it can also affect other parts of the body such as lymph nodes, skin and bones.

Diagnosis of tuberculosis, so allowing treatment, is the major weapon against the spread of the disease. Diagnosis may be made using a combination of clinical signs, sputum cultures, chest X-ray, histology of tissue and bronchial lavage fluid, and the use of the tuberculin skin test (also known as the Purified Protein Derivative Standard, or PPD skin test) such as the Mantoux test and Heaf Test. The tests rely on an immune reaction to *M. tuberculosis* protein, revealing the presence of antibodies of *M. tuberculosis* in the patient's blood.

The tests require administration of an immunological challenge to a patient, and a subsequent follow-up examination to determine the test result. These steps make the test difficult to apply for mass screening operations.

The present invention attempts to provide a solution to some of these problems.

SUMMARY OF THE INVENTION

In a broad first aspect, the invention comprises a peptide of fewer than 18 amino acids comprising the sequence NSPAX where X is Methionine (SEQ ID 18), Leucine (SEQ ID 17), Alanine (SEQ ID 15) or Valine (SEQ ID 10) wherein the peptide is capable of binding to an antibody raised against the peptide GRDIKVQFQSGGNNSPAV (SEQ ID 11). In particularly preferred embodiments, the peptide binds to such an antibody.

In practical terms, such an antibody would be raised against this peptide (SEQ ID 11) supplemented by an additional C amino acid at the C-terminal end, i.e. raised against GRDIKVQFQSGGNNSPAVC (SEQ ID 27).

In a second aspect, therefore, the peptide comprises up to 6 additional amino acids at the C and/or N terminal end of the sequence NSPAX (SEQ ID 28).

Preferably, therefore, the peptide of the first or second aspect comprises the sequence NNSPAX (SEQ ID 29), and more preferably the peptide comprises the sequence NNSPAV (SEQ ID 14).

In a further preferred aspect, the peptide comprises the sequence SGGNNSPAX (SEQ ID 26), where X is Methionine (SEQ ID 18), Leucine (SEQ ID 17), Alanine (SEQ ID 15) or Valine (SEQ ID 10).

In any aspect of the invention it is preferred that the peptide is not GRDIKVQFQSGGNNSPAV (SEQ ID 11).

Also in any aspect of the invention it is preferable that the peptide consists of the sequence SGGNNSPAX (SEQ ID 26), where X is Methionine (SEQ ID 18), Leucine (SEQ ID 17), Alanine (SEQ ID 15) or Valine (SEQ ID 10).

Also in any peptide of the invention it is preferable that X is Methionine (SEQ ID 18), Leucine (SEQ ID 17) or Alanine (SEQ ID 15). Especially preferred are peptides wherein X is Methionine (SEQ ID 18) or Alanine (SEQ ID 15). These particular substitutions are found to have particularly good Leu-heat stability, making them suitable for field use in hot countries.

Particularly preferred peptides according to any aspect of the invention further comprise a label. The use of a labelled peptide facilitates its use in an assay for the detection of *Mycobacterium tuberculosis*. Suitable labels might include radio-labels (e.g. by the addition of a radioactive species or the substitution of one or more atoms of the peptide by its radioactive equivalent) thereby allowing the presence or concentration of the peptide, or a complex comprising the peptide, to be readily detected, e.g. by scintillation counting or the like. Other labels such as an enzyme-mediated chromogenic label might also be used. Particularly preferred labels would be fluorescent labels, including binding of the peptide to a fluorescent protein. A fluorescent label such as Alexa Fluor (e.g. Alexa Fluor 633) is, however, particularly suitable.

Preferably also, any of the above peptides are in an isolated form, i.e. essentially free of proteins of native (e.g. bacterial, fungal or mammalian) origin.

Peptides described above have application in assays for the detection of *Mycobacterium tuberculosis*.

Included within the scope of the invention is a nucleotide sequence encoding any of the above peptides. Such a sequence has application in the biosynthesis of the peptides of the present invention.

Included within the scope of the invention is an antibody raised against SEQ ID 11. The antibodies of the invention may be polyclonal or monoclonal, or may be recombinant antibodies, such as chimeric antibodies wherein the murine constant regions on light and heavy chains are replaced by human sequences, or CDR-grafted antibodies wherein only the complementary determining regions are e.g. of murine origin. Antibodies of the invention may also be human antibodies prepared, for example, by immunization of transgenic animals capable of producing human antibodies (see, for example, PCT Application No. WO93/12227).

Also included within the scope of the invention is a displacement ELISA (Enzyme-Linked Immuno-Sorbent) assay for determining the presence of *Mycobacterium tuberculosis* comprising a peptide as described herein. A suitable procedure for carrying out such an assay will be described below. Preferably, such a displacement assay further comprises an antibody raised against SEQ ID 11, or a fragment of such an antibody having affinity for SEQ ID 11.

Also included within the scope of the invention is an ELISA assay for determining the presence of *Mycobacterium tuberculosis* comprising an antibody raised against SEQ ID 11, or a fragment of such an antibody having affinity for SEQ ID 11.

Further included within the scope of the invention is a displacement assay for determining the presence of *Mycobacterium tuberculosis* comprising a peptide according to the invention and a peptide according to SEQ ID 11.

BRIEF DESCRIPTION OF THE DRAWINGS

FIGS. 2(a) and 2(b) show results from an epitope mapping ELISA.

TEST DEVELOPMENT AND DESCRIPTION OF PREFERRED EMBODIMENTS

The test is based upon the identified T-cell epitope from *M. tuberculosis* Ag85B [Mustafa, A. S. et al, "Identification and HL Restriction of Naturally Derived Th1-Cell Epitopes from the Secreted 1-Cell Epitopes from the Secreted *Mycobacterium tuberculosis* Antigen 85B Recognised by Antigen-Specific Human CD4$^+$ T-Cell Lines", Infection and Immunity, 68(7), 3933-3940, 2000] represented by the 18-mer peptide p3 (Amino acids 19 to 36, denoted P779) with the sequence GRDIKVQFQSGGNNSPAV (SEQ ID 11).

An aspect of the invention is the provision of a competitive displacement ELISA (enzyme-linked immunosorbent assay) assay—effectively a ligand displacement assay. Antibodies to *M. tuberculosis*, particularly those directed towards the Ag85B epitope, are bound to a test plate. Peptides capable of binding to the antibodies, but with a lower affinity than the *M. tuberculosis* antigen are bound to the antibodies, preferably labelled with e.g. a fluorescent marker. When samples containing *M. tuberculosis* antigens (e.g. the organism itself) are brought into contact with the antibody-peptide complex, the antigens displace the peptides, which can be detected by a change in fluorescence. In another aspect of the invention, suitable synthetic peptides are provided, as described below:

Overlapping 10×9-mer peptides were synthesized, mapping the p3 18-mer (i.e. 1-9aa, 2-10aa, 3-11aa etc. of SEQ ID 11) to identify a target antigen to be utilized for the generation of the analogue library.

The sequences of the 10×9-mer peptides are shown below, using standard 1 letter amino acid coding:

```
SEQ ID 1:
GRDIKVQFQ (1-9aa), denoted P782-1

SEQ ID 2:
RDIKVQFQS (2-10aa), denoted P782-2

SEQ ID 3:
DIKVQFQSG (3-11aa), denoted P782-3

SEQ ID 4:
IKVQFQSGG (4-12aa), denoted P782-4

SEQ ID 5:
KVQFQSGGN (5-13aa), denoted P782-5

SEQ ID 6:
VQFQSGGNN (6-14aa), denoted P782-6

SEQ ID 7:
QFQSGGNNS (7-15aa), denoted P782-7

SEQ ID 8:
FQSGGNNSP (8-16aa), denoted P782-8

SEQ ID 9:
QSGGNNSPA (9-17aa), denoted P782-9

SEQ ID 10:
SGGNNSPAV (10-18aa), denoted P782-10
```

These peptides, along with the p3 18-mer (SEQ ID 11) were screened against antisera (from rabbit) to the p3 18-mer (SEQ ID 11). The screen utilized the competitive ELISA (Enzyme-linked immunosorbant assay) technique, which was used to assess the relative binding affinities of the 9-mer peptides to the 18-mer peptide.

Briefly, the assay involved binding (coating) the p3 18-mer (P779, SEQ ID 11) to ELISA plates, followed by incubation with variables amounts of competing ligand (9-mers, SEQ ID 1-10) with the antisera (1:250 dilution). The level of binding of the antisera to p3 18-mer (P779, SEQ ID 11) was indicated by treatment with goat anti-rabbit peroxidase conjugated antibody and then by addition of a chromogenic substrate ABTS (2,2-azino-di-[3-ethylbenzthiazoline sulphonate]) and hydrogen peroxide where upon a green colour developed which was recorded as an optical density (absorbance) on a plate reader. The colour development is proportional to the level of binding of the primary antisera bound to the plate.

A test ELISA was performed in order to ascertain the concentrations of coating peptide and competing peptides for the ELISA experiments, comprising a competitive ELISA of 9-mer P782-1 (GRDIKVQFQ)—SEQ ID 1—against 18-mer P779 (GRDIKVQFQSGGNNSPAV)—SEQ ID 11 (Mustafa, A. S. et al, supra). This 9-mer was chosen as it also overlaps with the p2 18-mer (YLQVPSPSMGRDIKVQFQ)—SEQ ID 12. From the results, the inventors showed the concentrations of peptides used were suitable for the ELISA studies. ELISA plates were coated with 2 μM solution of p3 18-mer (P779)—SEQ ID 11—and used 500 μM solutions of competing peptides, which were then subjected to four-fold serial dilution. Results from the test ELISA are shown in FIG. 1.

An Epitope Mapping ELISA was then performed, to determine relative binding affinities between the 10×9-mers (P782-1 to P782-10)—SEQ ID 1 to 10—against the p3 18-mer (P779)—SEQ ID 11. The peptide concentration range selected (linear part of the competition curve) is important to get a qualitative assessment of the relative binding affinities of the competing epitopes. The results showed that 9-mers P782-1 to P782-9 (i.e. SEQ ID 1 to 9) did not appear to bind to the antisera to any significant extent in this concentration range; however the 9-mer P782-10 (SGGNNSPAV)—SEQ ID 10—bound to the antisera as tightly as the p3 18-mer peptide (SEQ ID 11). This result is very significant and directed the inventors towards the possible importance of the C-terminal valine residue, as the preceding 9-mer P782-9 (QSGGNNSPA), SEQ ID 9, showed no significant binding even though it overlaps the P782-10 peptide, SEQ ID 10, by 8 residues. Results from this Epitope Mapping ELISA are shown in FIGS. 2(*a*) and 2(b).

A Targeted Epitope ELISA was then designed to test the importance of the C-terminal region of the epitope on binding to the antisera. Two 6-mers were synthesized, P782-11 (GNNSPA)—SEQ ID 13—and P782-12 (NNSPAV)—SEQ ID 14, which are truncated forms of their respective 9-mers and subjected these to competitive ELISA as before and also re-tested the 9-mer P782-10 (SEQ ID 10) identified as a significant epitope in the Epitope Mapping ELISA. Results from the Targeted Epitope ELISA are shown in FIG. 3. The data very clearly show reproducible results, and again indicated that:

The 9-mer P782-10 (SEQ ID 10) bound to the antisera as tightly as the p3 18-mer peptide P779 (SEQ ID 11)

The 6-mer P782-11 (SEQ ID 13) did not bind to the antisera and:

The 6-mer P782-12 (NNSPAV) (SEQ ID 14) binds to the antisera 2-fold (1.99) less tightly relative to either 9-mer P782-10 (SEQ ID 10) or 18-mer P779 (SEQ ID 11).

This result shows the importance of the C-terminal region that contains the valine residue. On the basis of this experiment it would be unwise to modify the N-terminal region but instead to target the C-terminal valine residue in order to generate some differing binding affinities. The inventors therefore decided to focus the library based upon the 9-mer P782-10 (SGGNNSPAV), SEQ ID 10, and to modify the C-terminal region and synthesised peptides with the sequence SGGNNSPA-X where X is a variable amino acid including other hydrophobic and charged amino acids.

For the Library ELISA the inventors synthesized the following peptides:

```
SEQ ID 15:
SGGNNSPAA, denoted P783-1

SEQ ID 16:
SGGNNSPAF, denoted P783-2

SEQ ID 17:
SGGNNSPAL, denoted P783-3

SEQ ID 18:
SGGNNSPAM, denoted P783-4

SEQ ID 19:
SGGNNSPAY, denoted P783-5

SEQ ID 20:
SGGNNSPAG, denoted P783-6

SEQ ID 21:
SGGNNSPAS, denoted P783-7

SEQ ID 22:
SGGNNSPAP, denoted P783-8

SEQ ID 23:
SGGNNSPAN, denoted P783-9

SEQ ID 24:
SGGNNSPAE, denoted P783-10

SEQ ID 25:
SGGNNSPAR, denoted P783-11
```

Figure 1:
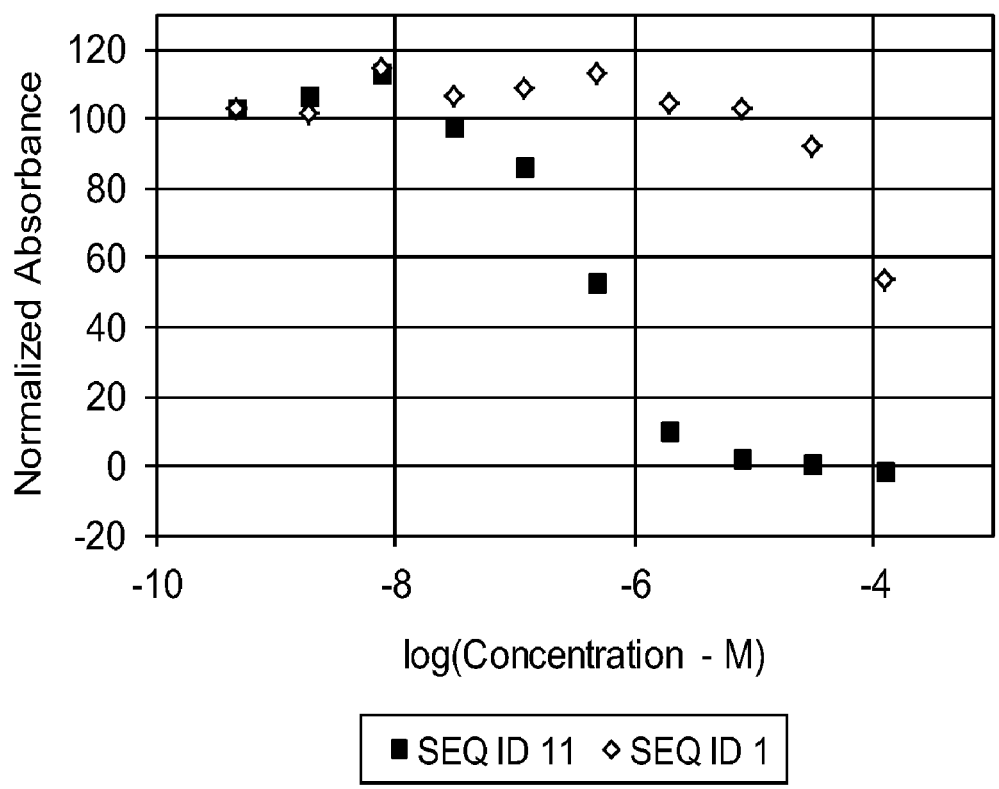
FIG. 1 shows results from a test ELISA to ascertain the concentrations of coating and competing peptides.
Figure 2A:
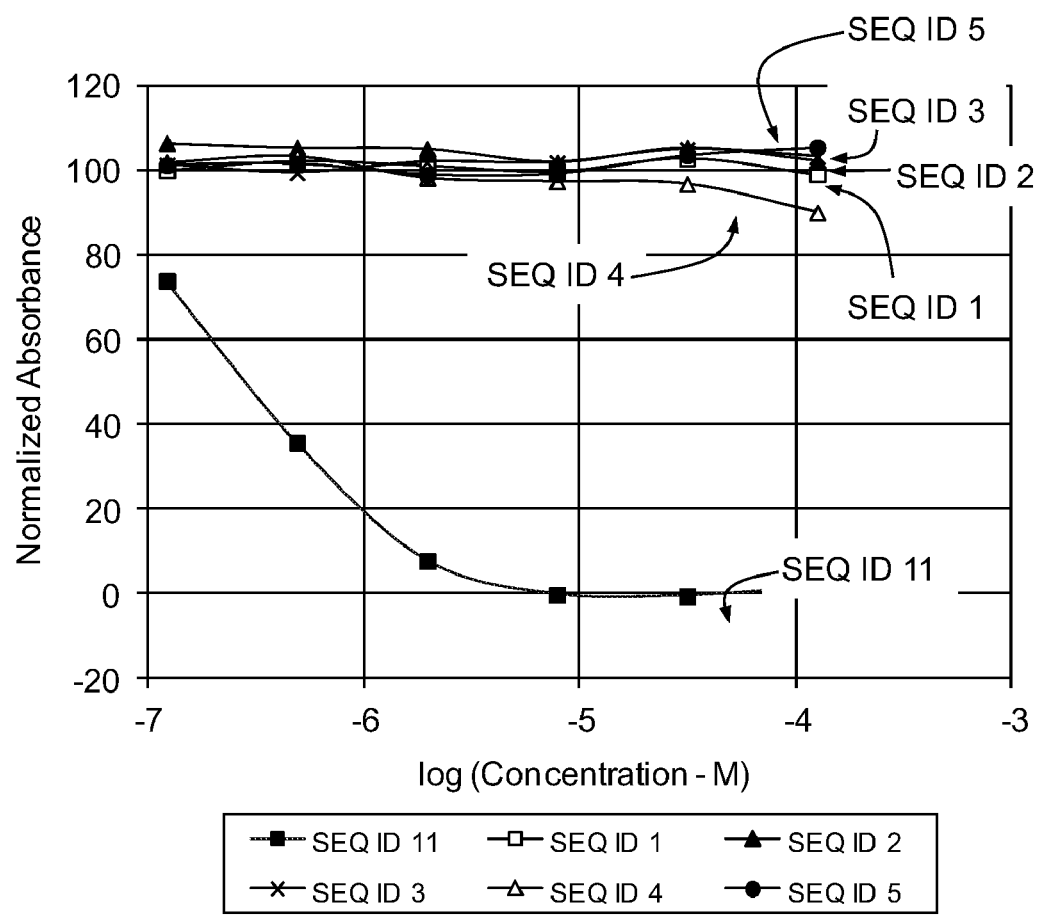
Figure 3:
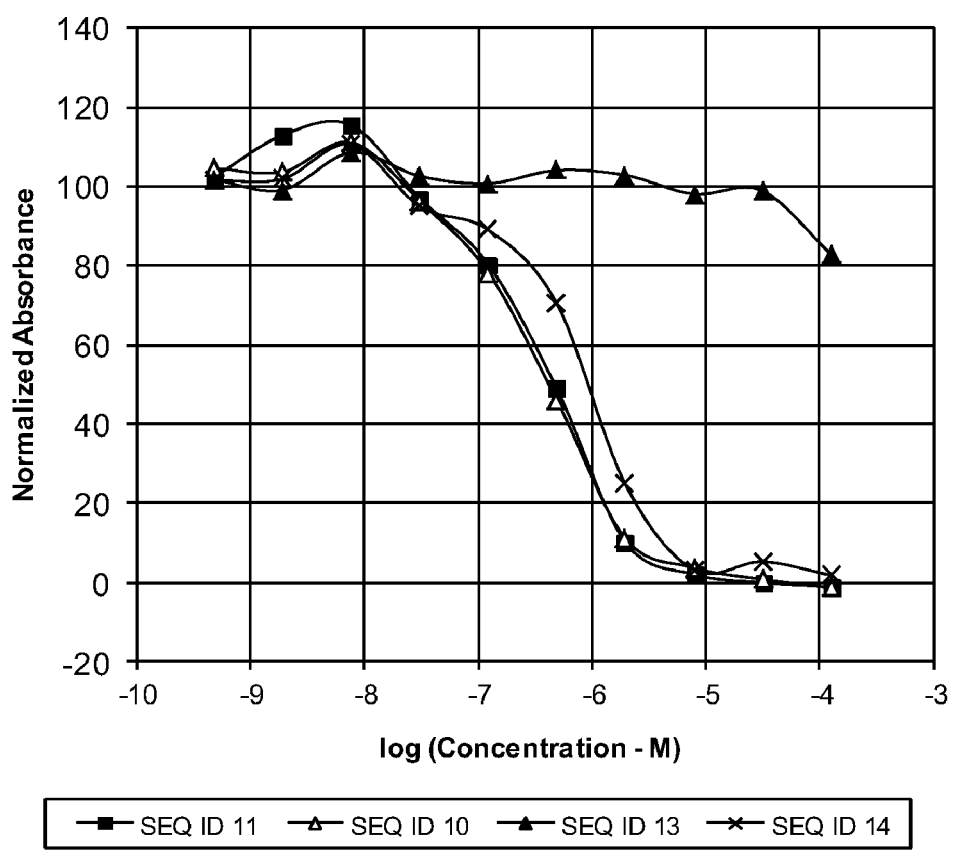
FIG. 3 shows results from a targeted epitope ELISA.
Figure 4:
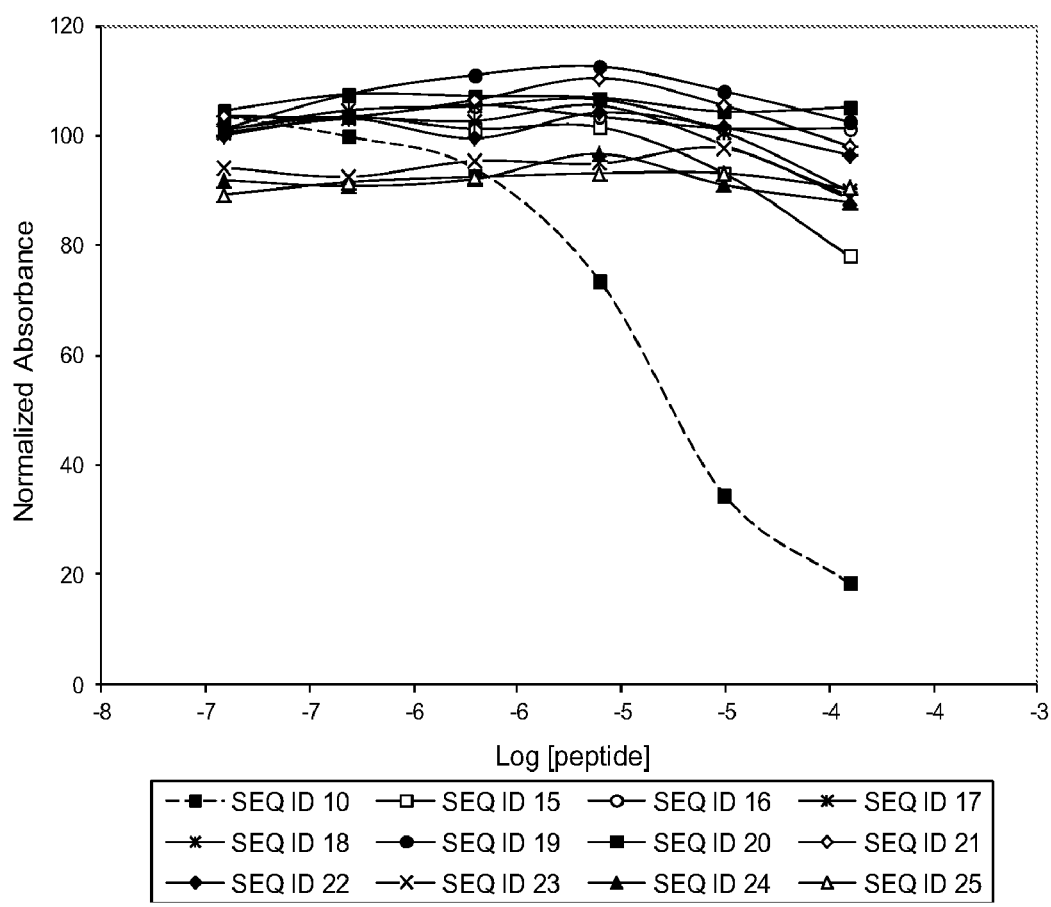
FIG. 4 shows results from a competitive ELISA showing binding affinities relative to the 9-mer SGGNNSPAV (SEQ ID 10).

The inventors restricted the concentrations of the competing peptides within that utilised in the previous experiments, as it would not be possible to assess the relative binding affinities of the competing peptides within a single assay. The results from the competitive ELISA of the library (shown graphically in FIG. 4) shows a range of binding affinities relative to the 9-mer P782-10 (SGGNNSPAV), SEQ ID 10. The epitopes of particular significance are the alanine, leucine and methionine variants (SEQ ID 15, 17 and 18) especially at epitope concentrations of 125 µM and 31.3 µM. Of these, the alanine and methionine variants are particularly preferred, as they have increased heat stability, making them particularly useful for field use in hot countries.

ELISA Assay

A suitable method for carrying out an ELISA assay according to the present invention is as follows:

In order to determine the presence or absence of *Mycobacterium tuberculosis* a sample from a patient is contacted with an antibody raised against SEQ ID 11; the presence or absence of a complex formed between a peptide in the sample and said antibody is detected; and the amount of complex formed in said sample to a normal control, is detected, wherein an increase in the amount of complex in the sample compared to the control indicates the presence of *Mycobacterium tuberculosis*. General methods of performing ELISA assays are known to the skilled addressee. Samples from patients may be provided in the form of body fluids such as blood, saliva, semen and milk or tissue samples such as biopsy material suitably prepared by e.g. homogenization. However, samples having origin from the respiratory tract are preferred. Of particular preference are sputum, or fluids obtained by bronchial or pulmonary lavage. Most preferred, however, are samples obtained by inducing a cough reflex in a patient by nebulization and collecting entrained material from a patient's breath; these samples contain material of tracheal origin.

Displacement ELISA Assay

A suitable method for carrying out a displacement ELISA assay according to the present invention is as follows:

In order to determine the presence or absence of *Mycobacterium tuberculosis*, a composition containing a peptide as described herein, and defined according to the claims, and a sample from a patient is provided. The composition is contacted with an antibody raised against SEQ ID 11; the presence or absence of a complex formed between said peptide and said antibody is detected; and the amount of complex formed in said sample is compared to a normal control, wherein an decrease in the amount of complex in the sample compared to the control indicates the presence of *Mycobacterium tuberculosis.*

General methods of performing displacement ELISA assays are known to the skilled addressee. Again, samples from patients may be provided in the form of body fluids such as blood, saliva, semen and milk or tissue samples such as biopsy material suitably prepared by e.g. homogenization. However, samples having origin from the respiratory tract are preferred. Of particular preference are sputum, or fluids obtained by bronchial or pulmonary lavage. Most preferred, however, are samples obtained by inducing a cough reflex in a patient by nebulization and collecting entrained material from a patient's breath; these samples contain material of tracheal origin.

The invention claimed is:

1. A peptide consisting of any of the following sequences:

SGGNNSPAA; (SEQ ID 15)

SGGNNSPAL; (SEQ ID 17)

SGGNNSPAM. (SEQ ID 18)

2. A peptide according to claim 1, further comprising a label.

3. An antibody that specifically binds to SEQ ID 11, or a fragment of said antibody, wherein the said fragment specifically binds to SEQ ID 11.

* * * * *

UNITED STATES PATENT AND TRADEMARK OFFICE
CERTIFICATE OF CORRECTION

PATENT NO.        : 8,372,412 B2                                             Page 1 of 1
APPLICATION NO.   : 12/158781
DATED             : February 12, 2013
INVENTOR(S)       : Sharma et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1270 days.

Signed and Sealed this
First Day of September, 2015

Michelle K. Lee
*Director of the United States Patent and Trademark Office*

```
                         SEQUENCE LISTING

<160> NUMBER OF SEQ ID NOS: 26

<210> SEQ ID NO 1
<211> LENGTH: 9
<212> TYPE: PRT
<213> ORGANISM: Mycobacterium tuberculosis

<400> SEQUENCE: 1

Gly Arg Asp Ile Lys Val Gln Phe Gln
1               5

<210> SEQ ID NO 2
```

```
<211> LENGTH: 9
<212> TYPE: PRT
<213> ORGANISM: Mycobacterium tuberculosis

<400> SEQUENCE: 2

Arg Asp Ile Lys Val Gln Phe Gln Ser
1               5

<210> SEQ ID NO 3
<211> LENGTH: 9
<212> TYPE: PRT
<213> ORGANISM: Mycobacterium tuberculosis

<400> SEQUENCE: 3

Asp Ile Lys Val Gln Phe Gln Ser Gly
1               5

<210> SEQ ID NO 4
<211> LENGTH: 9
<212> TYPE: PRT
<213> ORGANISM: Mycobacterium tuberculosis

<400> SEQUENCE: 4

Ile Lys Val Gln Phe Gln Ser Gly Gly
1               5

<210> SEQ ID NO 5
<211> LENGTH: 9
<212> TYPE: PRT
<213> ORGANISM: Mycobacterium tuberculosis

<400> SEQUENCE: 5

Lys Val Gln Phe Gln Ser Gly Gly Asn
1               5

<210> SEQ ID NO 6
<211> LENGTH: 9
<212> TYPE: PRT
<213> ORGANISM: Mycobacterium tuberculosis

<400> SEQUENCE: 6

Val Gln Phe Gln Ser Gly Gly Asn Asn
1               5

<210> SEQ ID NO 7
<211> LENGTH: 9
<212> TYPE: PRT
<213> ORGANISM: Mycobacterium tuberculosis

<400> SEQUENCE: 7

Gln Phe Gln Ser Gly Gly Asn Asn Ser
1               5

<210> SEQ ID NO 8
<211> LENGTH: 9
<212> TYPE: PRT
<213> ORGANISM: Mycobacterium tuberculosis

<400> SEQUENCE: 8

Phe Gln Ser Gly Gly Asn Asn Ser Pro
1               5

<210> SEQ ID NO 9
<211> LENGTH: 9
<212> TYPE: PRT
<213> ORGANISM: Mycobacterium tuberculosis
```

```
<400> SEQUENCE: 9

Gln Ser Gly Gly Asn Asn Ser Pro Ala
1               5

<210> SEQ ID NO 10
<211> LENGTH: 9
<212> TYPE: PRT
<213> ORGANISM: Mycobacterium tuberculosis

<400> SEQUENCE: 10

Ser Gly Gly Asn Asn Ser Pro Ala Val
1               5

<210> SEQ ID NO 11
<211> LENGTH: 18
<212> TYPE: PRT
<213> ORGANISM: Mycobacterium tuberculosis

<400> SEQUENCE: 11

Gly Arg Asp Ile Lys Val Gln Phe Gln Ser Gly Gly Asn Asn Ser Pro
1               5                   10                  15

Ala Val

<210> SEQ ID NO 12
<211> LENGTH: 18
<212> TYPE: PRT
<213> ORGANISM: Mycobacterium tuberculosis

<400> SEQUENCE: 12

Tyr Leu Gln Val Pro Ser Pro Ser Met Gly Arg Asp Ile Lys Val Gln
1               5                   10                  15

Phe Gln

<210> SEQ ID NO 13
<211> LENGTH: 6
<212> TYPE: PRT
<213> ORGANISM: Mycobacterium tuberculosis

<400> SEQUENCE: 13

Gly Asn Asn Ser Pro Ala
1               5

<210> SEQ ID NO 14
<211> LENGTH: 6
<212> TYPE: PRT
<213> ORGANISM: Mycobacterium tuberculosis

<400> SEQUENCE: 14

Asn Asn Ser Pro Ala Val
1               5

<210> SEQ ID NO 15
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 15

Ser Gly Gly Asn Asn Ser Pro Ala Ala
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 16

Ser Gly Gly Asn Asn Ser Pro Ala Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 17

Ser Gly Gly Asn Asn Ser Pro Ala Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 18

Ser Gly Gly Asn Asn Ser Pro Ala Met
1               5

<210> SEQ ID NO 19
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 19

Ser Gly Gly Asn Asn Ser Pro Ala Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 20

Ser Gly Gly Asn Asn Ser Pro Ala Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 21
```

```
Ser Gly Gly Asn Asn Ser Pro Ala Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 22

Ser Gly Gly Asn Asn Ser Pro Ala Pro
1               5

<210> SEQ ID NO 23
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 23

Ser Gly Gly Asn Asn Ser Pro Ala Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 24

Ser Gly Gly Asn Asn Ser Pro Ala Glu
1               5

<210> SEQ ID NO 25
<211> LENGTH: 9
<212> TYPE: PRT
<213> ORGANISM: Artificial Sequence
<220> FEATURE:
<223> OTHER INFORMATION: Modification (at position 9) of native
      Mycobacterium tuberculosis sequence

<400> SEQUENCE: 25

Ser Gly Gly Asn Asn Ser Pro Ala Arg
1               5

<210> SEQ ID NO 26
<211> LENGTH: 9
<212> TYPE: PRT
<213> ORGANISM: Artificial Sequence
<220> FEATURE:
<223> OTHER INFORMATION: Modification (at position 9) of Mycobacterium
      tuberculosis sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 26

Ser Gly Gly Asn Asn Ser Pro Ala Xaa
1               5
```